United States Patent
Tamura et al.

(10) Patent No.: US 12,053,716 B2
(45) Date of Patent: Aug. 6, 2024

(54) TREATMENT APPARATUS FOR WASTE CLEANING LIQUID AND TREATMENT METHOD FOR WASTE CLEANING LIQUID

(71) Applicants: MITSUBISHI CHEMICAL ENGINEERING CORPORATION, Chuo-ku (JP); LG Energy Solution Nanjing Co., Ltd., Nanjing (CN)

(72) Inventors: Takahiro Tamura, Chuo-ku (JP); Yotaro Nishijima, Chuo-ku (JP); Yuan Tang, Chuo-ku (JP); Nanri Fang, Nanjing (CN)

(73) Assignees: MITSUBISHI CHEMICAL ENGINEERING CORPORATION, Chuo-ku (JP); LG Energy Solution Nanjing Co., Ltd., Nanjing (CN)

( * ) Notice: Subject to any disclaimer, the term of this patent is extended or adjusted under 35 U.S.C. 154(b) by 188 days.

(21) Appl. No.: 17/767,578

(22) PCT Filed: Sep. 29, 2020

(86) PCT No.: PCT/JP2020/036992
§ 371 (c)(1),
(2) Date: Apr. 8, 2022

(87) PCT Pub. No.: WO2021/070689
PCT Pub. Date: Apr. 15, 2021

(65) Prior Publication Data
US 2022/0410027 A1  Dec. 29, 2022

(30) Foreign Application Priority Data

Oct. 9, 2019 (JP) .............................. 2019-186434
Sep. 23, 2020 (JP) .............................. 2020-159055

(51) Int. Cl.
*B01D 1/22* (2006.01)
*C02F 1/04* (2023.01)
*C02F 101/38* (2006.01)

(52) U.S. Cl.
CPC .............. *B01D 1/225* (2013.01); *C02F 1/048* (2013.01); *C02F 2101/38* (2013.01); *C02F 2301/046* (2013.01)

(58) Field of Classification Search
CPC ...... B01D 1/225; C02F 1/048; C02F 2101/38; C02F 2301/046
See application file for complete search history.

(56) References Cited

U.S. PATENT DOCUMENTS 9,755,223 B2 * 9/2017 Hamada ................. H01M 4/36
10,766,788 B2 * 9/2020 Tian ........................ C02F 1/048
(Continued)

FOREIGN PATENT DOCUMENTS

CN  107768764 A  3/2018
CN  208038082 U  11/2018
(Continued)

OTHER PUBLICATIONS

Machine Translation of CN208038082U from IP Com obtained Dec. 5, 2023. (Year: 2023).*
(Continued)

*Primary Examiner* — Jonathan Miller
(74) *Attorney, Agent, or Firm* — Oblon, McClelland, Maier & Neustadt, L.L.P.

(57) ABSTRACT

Provided are a treatment apparatus and a treatment method treating a waste cleaning liquid discharged from a process of producing an electrode of a lithium-ion secondary battery, in which a liquid component and a solid component are efficiently separated from each other, and the liquid component can be sufficiently collected and subjected to volume reduc-
(Continued)

tion treatment. The treatment apparatus includes: a stirring tank stirring the waste cleaning liquid; a liquid feed line that takes out the waste cleaning liquid from the stirring tank; and a thin film evaporator evaporating a cleaning liquid in the waste cleaning liquid to separate the solid component. Then, in the treatment method, the waste cleaning liquid is stirred in the stirring tank, the waste cleaning liquid is supplied to the thin film evaporator in a state in which the solid component is diffused, and the cleaning liquid in the waste cleaning liquid is evaporated.

8 Claims, 3 Drawing Sheets

(56) References Cited

U.S. PATENT DOCUMENTS

| | | | |
|---|---|---|---|
| 2005/0069820 A1* | 3/2005 | Nomura | G03C 5/3952 |
| | | | 430/398 |
| 2012/0241307 A1 | 9/2012 | Miyata et al. | |
| 2014/0377629 A1 | 12/2014 | Miyazaki et al. | |
| 2015/0367249 A1 | 12/2015 | Miyata et al. | |

FOREIGN PATENT DOCUMENTS

| | | | |
|---|---|---|---|
| CN | 208382938 U | | 1/2019 |
| JP | 2005-108531 A | | 4/2005 |
| JP | 2007-99690 A | | 4/2007 |
| JP | 2010-105257 A | | 5/2010 |
| JP | 2011-56484 A | | 3/2011 |
| JP | 2014226648 A | * | 12/2014 |
| JP | 2015-26603 A | | 2/2015 |
| JP | 2015-37778 A | | 2/2015 |
| WO | WO 2014/142314 A1 | | 9/2014 |

OTHER PUBLICATIONS

Machine Translation of JP 2014226648 A from IP Com obtained Dec. 6, 2023. (Year: 2023).*
Machine Translation of JP201537778A from IP Com obtained Dec. 5, 2023. (Year: 2023).*
International Search Report issued Dec. 8, 2020 in PCT/JP2020/036992 filed Sep. 29, 2020, 2 pages.
Combined Chinese Office Action and Search Report issued on Mar. 16, 2023 in Chinese Patent Application No. 202080070236.6 (with unedited computer-generated English translation), 17 pages.
Indian Office Action issued Aug. 8, 2022 in Indian Patent Application No. 202217026280, 5 pages.
Extended European Search Report issued on Sep. 19, 2022 in European Patent Application No. 20875392.1 , 7 pages.

* cited by examiner

TREATMENT APPARATUS FOR WASTE CLEANING LIQUID AND TREATMENT METHOD FOR WASTE CLEANING LIQUID

CROSS-REFERENCE TO RELATED APPLICATIONS

The present application is the national stage of international application PCT/JP2020/036992, filed on Sep. 29, 2020, and claims the benefit of the filing date of Japanese Appl. No. 2019-186434, filed on Oct. 9, 2019, and Japanese Appl. No. 2020-159055, filed on Sep. 23, 2020.

TECHNICAL FIELD

The present invention relates to a treatment apparatus for waste cleaning liquid and a treatment method for waste cleaning liquid. More specifically, the present invention relates to a treatment apparatus and a treatment method, which efficiently separate, into a liquid component and a solid component, a waste cleaning liquid discharged from a process of producing an electrode of a lithium-ion secondary battery, and facilitate a collection process.

BACKGROUND ART

In a process of producing an electrode of a lithium-ion secondary battery, a base material is coated with an electrode material constituted of: an active substance such as a lithium compound including lithium cobalt oxide, lithium manganate, and the like; a binder such as polyvinylidene fluoride; and N-methyl-2-pyrrolidone (hereinafter, abbreviated as "NMP") as a solvent. A resultant thus formed is calcined to produce a positive electrode. Further, a base material is coated with an electrode material constituted of; a lithium compound containing carbon, titanium or the like; a binder such as polyvinylidene fluoride; and water as a solvent. A resultant thus formed is calcined to produce a negative electrode.

Moreover, in such an electrode production process, a preparation tank for use in preparation is cleaned in conjunction with a preparation operation of the electrode material. In that case, the NMP is usually used as a cleaning liquid in a preparation tank in a positive electrode production process, and water is usually used as a cleaning liquid in a preparation tank in a negative electrode production process. Then, in a lot of cases, each of waste cleaning liquids discharged from these preparation tanks is contained in a portable container such as an intermediate bulk container (IBC), is conveyed to a treatment plant, and is disposed of there.

Incidentally, in such an electrode production process as described above, a large amount of the cleaning liquid is used for the electrode material to be cleaned and removed from the preparation tank, and a total amount of the generated waste cleaning liquid is conveyed by the portable container, and is disposed of. Accordingly, the treatment of the waste cleaning liquid largely affects electrode production cost. Hence, in the electrode production process, desirably, the waste liquid is reduced in volume as much as possible by separating the electrode material that is a solid component from the waste cleaning liquid, and further, the NMP used as the cleaning liquid is collected.

The waste cleaning liquid discharged from the electrode production process is a suspension of the cleaning liquid and the electrode material, and treatment by evaporation separation is conceived in order to separate such a liquid component and such a solid component. Then, as the separation treatment by evaporation, for example, there are a method using such a distillation apparatus as for use also in purifying the NMP (refer to Patent Literature 1), a method using a thin film evaporator (refer to Patent Literature 2), and the like.

CITATION LIST

Patent Literature

Patent Literature 1: JP 2011-56484 A
Patent Literature 2: JP 2007-99690 A

SUMMARY OF INVENTION

Technical Problem

The waste cleaning liquid discharged from the process of producing an electrode of a lithium-ion secondary battery is such a suspension as described above, in which the solid component is easy to precipitate due to a large specific gravity thereof. Accordingly, when the separation treatment is attempted by evaporation, blockages occur in flow paths, instruments and the like, through which the waste cleaning liquid is introduced to an evaporation device, and in an instrument and the like in the evaporation device, and actually, there occurs a problem that it is difficult to treat the waste cleaning liquid smoothly and continuously. Hence, in the electrode production process, desired is an achievable technique capable of surely separating the liquid component and the solid component from each other.

The present invention has been made in view of the above-described actual circumstances. It is an object of the present invention to provide a treatment apparatus and a treatment method, which treat the waste cleaning liquid discharged from the process of producing an electrode of a lithium-ion secondary battery, in which the liquid component and the solid component are efficiently separated from each other, the liquid component can be sufficiently collected, and the waste liquid can be subjected to volume reduction treatment.

Solution to Problem

In order to solve the above-described problem, in the present invention, when the waste cleaning liquid discharged from the electrode production process is supplied to evaporation separating means to separate the solid component by evaporation, the waste cleaning liquid is stirred in advance by stirring means to evenly diffuse the solid component, and is supplied to the evaporation separating means in a state in which the solid component is diffused, whereby the solid component is prevented from being retained and adhered in and to the flow paths and the devices. Further, when the waste cleaning liquid is supplied to the evaporation separating means, the waste cleaning liquid is heated up to a predetermined temperature in addition to the stirring of the waste cleaning liquid, whereby evaporation efficiency in the evaporation separating means is increased.

That is, the present invention is constituted of two aspects. A first aspect is that a treatment apparatus that treats a waste cleaning liquid discharged from a process of producing an electrode of a lithium-ion secondary battery, the waste cleaning liquid being a suspension of an electrode material that is a solid component and a cleaning liquid, the treatment apparatus including: stirring means for stirring the waste cleaning liquid introduced from the electrode production process; a liquid feed line that takes out the waste cleaning liquid from the stirring means; and evaporation separating means for evaporating the cleaning liquid in the waste cleaning liquid to separate the solid component, the evaporation separating means being supplied with the waste cleaning liquid by the liquid feed line, being characterized in that the waste cleaning liquid is supplied to the evaporation separating means by the liquid feed line while stirring the waste cleaning liquid by the stirring means.

Moreover, a second aspect of the present invention is a waste cleaning liquid treatment method of treating, by a treatment apparatus, a waste cleaning liquid discharged from a process of producing an electrode of a lithium-ion secondary battery, the waste cleaning liquid being a suspension of an electrode material that is a solid component and a cleaning liquid, being characterized in that the treatment apparatus includes: stirring means for stirring the waste cleaning liquid introduced from the electrode production process; a liquid feed line that takes out the waste cleaning liquid from the stirring means; and evaporation separating means for evaporating the cleaning liquid in the waste cleaning liquid to separate the solid component, the evaporation separating means being supplied with the waste cleaning liquid by the liquid feed line, and in the treatment method, the waste cleaning liquid is stirred by the stirring means, the waste cleaning liquid is supplied to the evaporation separating means in a state in which the solid component is diffused, and in the evaporation separating means, the cleaning liquid in the waste cleaning liquid is evaporated to separate the solid component.

Advantageous Effects of Invention

In accordance with the present invention, the waste cleaning liquid is supplied to the evaporation separating means in a state in which the solid component is diffused. Accordingly, the blockages in the flow paths and the instruments due to the solid component can be prevented. Moreover, the waste cleaning liquid is heated up to a predetermined temperature in addition to the stirring of the waste cleaning liquid, whereby the evaporation efficiency by the evaporation separating means can be further increased. Accordingly, separation efficiency of the liquid component and the solid component can be increased, and a high-boiling-point component and a peroxide can be suppressed from being generated. Then, in accordance with the present invention, the volume reduction treatment of the waste liquid becomes possible, and accordingly, production cost of the electrode can be further reduced.

DESCRIPTION OF EMBODIMENTS

Figure 1:
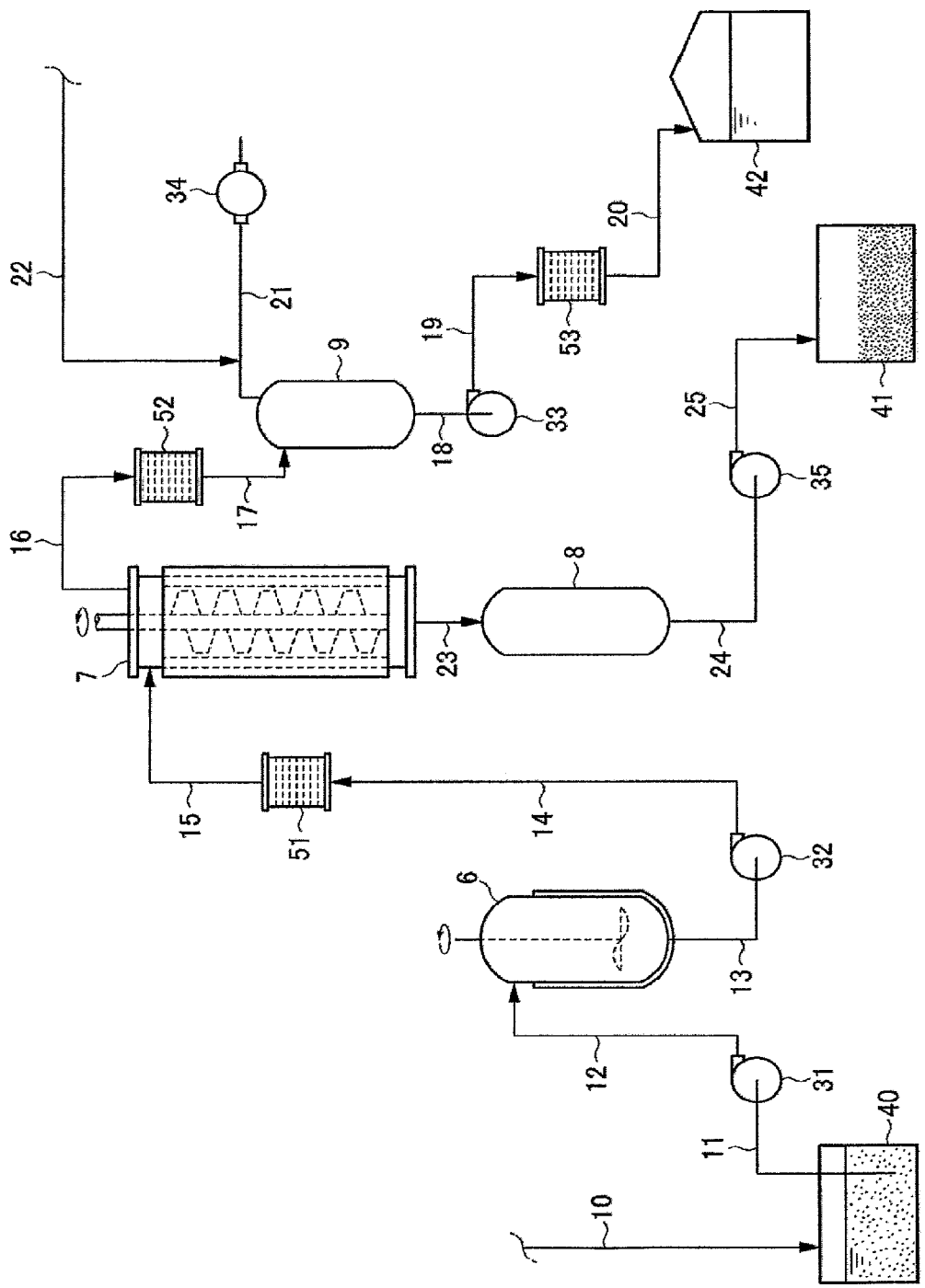
FIG. 1 is a flow diagram showing a main configuration of a treatment method for waste cleaning liquid and a treatment apparatus for waste cleaning liquid according to the present invention.

Referring to the drawings, a description will be given of an embodiment of a treatment apparatus for waste cleaning liquid (hereinafter, abbreviated as a "treatment apparatus") according to the present invention and a treatment method for waste cleaning liquid using the treatment apparatus (hereinafter, abbreviated as a "treatment method") according to the present invention.

The present invention is applied in order to treat a waste cleaning liquid discharged from a process of producing an electrode of a lithium-ion secondary battery. The above-described waste cleaning liquid is a suspension of an electrode material that is a solid component and of a cleaning liquid, and the waste cleaning liquid discharged from a preparation tank in a positive electrode production process contains the NMP for use in cleaning as a main component, and a solid component and a binder contained in the electrode material. Moreover, a waste cleaning liquid discharged from a preparation tank in a negative electrode production process includes water for use in cleaning as a main component, and a solid component and a binder contained in the electrode material.

Figure 2:
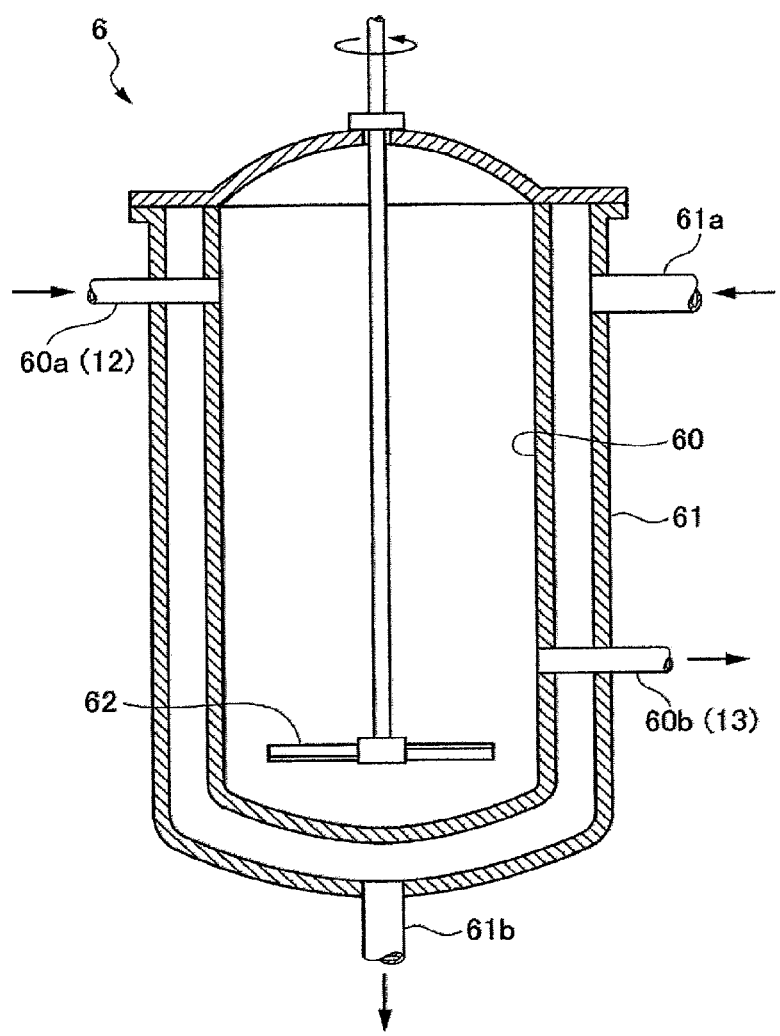
FIG. 2 is a longitudinal cross-sectional view showing a structure of a stirring tank as an example of stirring means for use in the present invention.
Figure 3:
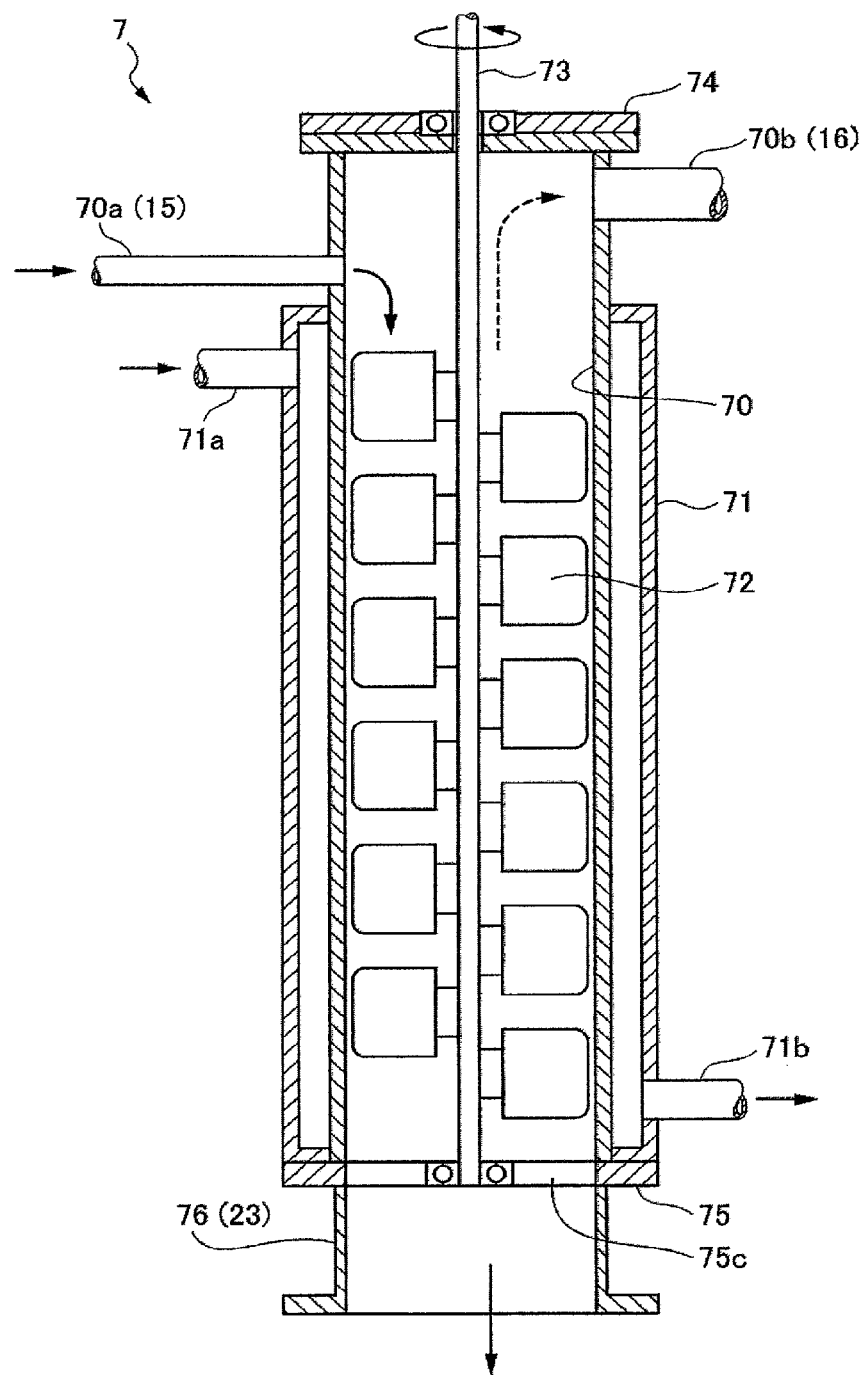
FIG. 3 is a longitudinal cross-sectional view showing a structure of an example of a thin film evaporator as evaporation separating means for use in the present invention.

First, the treatment apparatus of the present invention will be described. The treatment apparatus of the present invention is applied for each of the waste cleaning liquids discharged from the respective electrode production steps. In the following embodiment, a description will be given of an example of the treatment apparatus applied to the treatment of the waste cleaning liquid that is discharged from the positive electrode production process and contains the NMP. Note that, in FIGS. 1 to 3 showing the treatment apparatus, valves, a thermometer, a liquid level gauge and a control device are omitted.

As shown in FIG. 1, the treatment apparatus of the present invention includes: stirring means for stirring the-waste cleaning liquid introduced from the electrode production process; a liquid feed line that takes out the waste cleaning liquid from the stirring means; and evaporation separating means for evaporating the cleaning liquid in the waste cleaning liquid to separate the solid component, the evaporation separating means being supplied with the waste cleaning liquid by the liquid feed line, in which the waste cleaning liquid is supplied to the evaporation separating means by the liquid feed line while stirring the waste cleaning liquid by the stirring means.

In usual, in a subsequent stage to the electrode production process, the waste cleaning liquid is reserved in a conventional portable container 40 from a preparation tank (not shown) of a coating apparatus through a flow path 10 for discharging the waste cleaning liquid. Then, in the treatment apparatus, through a subject liquid supply line constituted of a flow path 11, a pump 31 and a flow path 12, the waste cleaning liquid is introduced into the above-described stirring means from the portable container 40.

As the stirring means, a stirring tank 6 as shown is mentioned. As will be described later, the stirring tank 6 is disposed in order to disperse the solid component in the waste cleaning liquid supplied to the above-described evaporation separating means. As the stirring tank 6, a tank having an appropriate structure can be used as long as it is provided with a stirring device such as a rotating wing or a screw capable of stirring the waste cleaning liquid. Further, preferably, the stirring tank 6 includes heating means in order to increase fluidity of the waste cleaning liquid supplied to the above-described evaporation separating means.

Specifically, as shown in FIG. 2, the stirring tank 6 includes: a tank body 60 having a stirring wing 62 therein; and a heating instrument, for example, a jacket 61 disposed on an outer circumferential portion of the tank body. The tank body 60 is a hermetically sealed container with an approximate internal capacity of 5 to 20 m³, is provided, on an upper end side thereof, with a subject liquid inlet 60a into which the above-described flow path 12 is connected, and is provided, on a lower end side thereof, with a subject liquid outlet 60b into which a flow path 13 to be described later is connected. The stirring wing 62 disposed in a vicinity of a bottom portion of the tank body 60 is configured to be rotatable by a drive shaft inserted from an upper end of the tank body 60. The jacket 61 is a heating oven that circulates vapor as a heating medium on the outer circumferential portion of the tank body 60, is provided with a heating medium supply port 61a on an upper end portion thereof, and is provided with a heating medium discharge port (drain) 61b on a lower end portion thereof.

Further, though not shown, the stirring tank as the stirring means may include a stirring device with another structure. For example, in the tank body, the stirring tank may include a circulation line by a pump. Such a stirring device by a pump is constituted by connecting sequentially a flow path that drains the waste cleaning liquid from the bottom portion of the tank body, a pump and a flow path that recirculates the waste cleaning liquid to an upper portion of the tank body. Further, like the above-described stirring tank 6, preferably, the stirring tank includes heating means such as a jacket disposed on an outer circumferential portion of the tank body, and is constituted to be capable of heating the waste cleaning liquid in the above-described tank body. Further, as the stirring means, a screw pump that transfers the suspension while stirring the same, or the like can also be used.

Note that, as the heating means in the above-described stirring means, a variety of heat exchangers such as a heater disposed in the inside can be used as well as such an instrument as the jacket, which is disposed on the outer circumferential portion of the tank. Then, though not shown, the waste cleaning liquid is heated up to a predetermined temperature by the above-described heating means. For example, the temperature of the waste cleaning liquid in the tank body 60 is detected by a temperature sensor provided in the stirring tank 6 and the control device of the treatment apparatus, and the heating means is constituted to be capable of heating the waste cleaning liquid in the tank body 60 to 40 to 90° C., preferably 70 to 90° C.

As shown in FIG. 1, the above-described liquid feed line that takes out the waste cleaning liquid from the stirring tank 6 and supplies the same to the above-described evaporation separating means is constituted of the flow path 13, a pump 32, a flow path 14, and a flow path 15. Moreover, in order to increase the fluidity of the waste cleaning liquid supplied to the evaporation separating means and to approximate the temperature of the waste cleaning liquid to the evaporation temperature, preferably, the liquid feed line is added with a heating device 51 downstream of the pump 32, that is, between the flow path 14 and the flow path 15. By such a heating device 51, the waste cleaning liquid to be fed is made capable of being heated to 60 to 100° C., preferably 80 to 100° C. Note that a variety of heat exchangers including a spiral-type one can be used as the heating device 51.

Incidentally, in the case of collecting the waste cleaning liquid containing the NMP by evaporation, preferably, the waste cleaning liquid is evaporated at a temperature as low as possible and for a residence time as short as possible in order to suppress a high-boiling-point component and a peroxide from being generated. Accordingly, in the present invention, a thin film evaporator as an example, is used as the above-described evaporation separating means for evaporating the waste cleaning liquid and separating the solid component. The thin film evaporator is a known device that forms a thin film of a subject liquid on an evaporation surface and heats the same and performs purification, enrichment and the like of the subject liquid. In usual, the thin film evaporator is operated under a reduced pressure condition, and can evaporate a liquid component at a relatively low temperature. Specifically, the downflow-type thin film evaporator 7 shown in FIG. 3 is used as such a thin film evaporator.

The thin film evaporator 7 shown in FIG. 3 includes: a cylindrical evaporator body 70 supplied with the waste cleaning liquid from one end portion thereof, a rotating blade 72 disposed along a centerline of the evaporator body; and heating means disposed on an outer circumferential portion of the evaporator body 70. The thin film evaporator 7 is provided with a structure to form a thin film of the waste cleaning liquid that is the subject liquid on an inner circumferential surface of the evaporator body 70, and to scrape off a remaining solid component by the rotating blade 72 and discharge them from other end portion of the evaporator body 70.

In the thin film evaporator 7, the evaporator body 70 is a metallic cylindrical container with an approximate heat transfer area of 2 to 10 m², and the inner circumferential surface thereof is used as the evaporation surface. An upper end portion of the evaporator body 70 is constituted as a subject liquid supply/discharge portion. The waste cleaning liquid is supplied through a subject liquid inlet 70a connected to the flow path 15, and the vapor (NMP) separated from the waste cleaning liquid is discharged through a vapor outlet 70b connected to the flow path 16.

The rotating blade 72 is disposed in a spiral shape as an example along a drive shaft 73 inserted into the center of the evaporator body 70, and a tip end portion of the rotating blade 72 is constituted in a state of substantially contacting the inner circumferential surface of the evaporator body 70. The drive shaft 73 is supported by a bearing provided in an upper lid 74 on the upper end of the evaporator body 70, and by a bearing provided in a bottom lid 75 on the lower end of the evaporator body 70. Moreover, the bottom lid 75 is provided with slits 75c which drop the solid component that is sludge downward, and the thin film evaporator 7 is constituted to discharge the solid component from a sludge discharge port 76 connected to a flow path 23 to be described later.

As the heating means on the outer circumferential portion of the evaporator body 70, in usual, used is a jacket 71 that circulates vapor as a heating medium. Like the above-mentioned stirring tank 6, the jacket 71 is a heating oven that circulates the vapor of the evaporator body 70, and is provided with a heating fluid inlet 71a on an upper end portion thereof, and is provided with a heating fluid outlet (drain) 71b on a lower end portion thereof.

As shown in FIG. 1, in the treatment apparatus, in order to reduce a pressure in a system thereof by a vacuum pump 34 to be described later, the solid component separated by the thin film evaporator 7 is taken out into a sludge collection container 8 through the flow path 23 and is tentatively reserved therein. Then, a flow path 24, a pump 35, and a flow path 25, which constitute an unloading line, are connected to a bottom portion of the sludge collection container 8. Through the unloading line, the solid component in the sludge collection container 8 is transferred to a portable container 41 for unloading.

Meanwhile, the above-mentioned flow path 16 as a vapor collection line is connected to the subject liquid supply/discharge portion of the above-described thin film evaporator 7, and a condenser 52 is disposed downstream of the flow path 16. Then, in the treatment apparatus, the vapor of the NMP separated by the thin film evaporator 7 is liquefied by the condenser 52, and the liquefied NMP is collected to a separated liquid collection container 9 through the flow path 17. Note that a variety of heat exchangers such as a multi-pipe-type heat exchanger can be used as the condenser 52.

Like the above-mentioned sludge collection container 8, the separated liquid collection container 9 is disposed in order to maintain the inside of the system in a pressure reduction state. A liquid withdrawal line constituted of a flow path 18, a pump 33, a flow path 19, a cooler 53, and a flow path 20 is connected to a bottom portion of the separated liquid collection container 9. In the treatment apparatus, the NMP in the separated liquid collection container 9 is stored in a collected liquid storage tank 42 through the liquid withdrawal line. The cooler 53 is disposed in order to cool, to room temperature, the NMP stored in the collected liquid storage tank 42. As the cooler 53, a variety of heat exchangers such as a multi-pipe-type heat exchanger can be used.

Moreover, in the treatment apparatus, in order to promote the evaporation in the thin film evaporator 7 by reducing the pressure in the system of the treatment apparatus itself, for example, an upper portion of the separated liquid collection container 9 is connected to the vacuum pump 34 through a flow path 21. Further, in order to prevent the invasion of air into the system, and to suppress the generation of the peroxide in the NMP, a flow path 22 for supplying inert gas such as nitrogen is connected, for example, to the above-described flow path 21.

Next, the treatment method of the present invention, which uses the above-described treatment apparatus, will be described. The waste cleaning liquid discharged from the electrode production process, for example, such a waste cleaning liquid that is discharged from the coating apparatus in the positive electrode production process and contains the NMP as a main component is reserved in the portable container 40 through the flow path 10.

In the treatment method of the present invention, first, the waste cleaning liquid in the portable container 40 is introduced into the stirring tank 6 as an example of stirring means through the flow path 11, the pump 31 and the flow path 12. An introduction amount of the waste cleaning liquid into the stirring tank 6 is set, for example, to 100 to 500 kg/hour though the introduction amount varies depending on a scale of the electrode production process. Moreover, when the treatment apparatus is operated, the vacuum pump 34 is actuated to reduce the pressure in the system to 1 to 10 kPaA while supplying nitrogen as an example into the system through the flow path 22.

Subsequently, when a liquid level of the waste cleaning liquid reaches a predetermined height in the stirring tank 6, the stirring wing 62 is rotated to stir the waste cleaning liquid, whereby the solid component in the waste cleaning liquid is diffused. Moreover, at the same time, the vapor for heating is supplied to the jacket 61 to heat the waste cleaning liquid in the stirring tank 6 to 40 to 90° C., preferably, 70 to 90° C. Thus, the fluidity of the waste cleaning liquid can be increased to approximate the temperature thereof to the evaporation temperature. Then, while being stirred in the stirring tank 6, the waste cleaning liquid is supplied to the thin film evaporator 7 as evaporation separating means through the flow path 13, the pump 32, the flow path 14 and the flow path 15, which constitute the liquid feed line.

Moreover, when the waste cleaning liquid is supplied to the thin film evaporator 7, then in the above-described liquid feed line, the waste cleaning liquid is further heated to 60 to 100° C., preferably 80 to 100° C. by the heating device 51. Thus, the fluidity of the waste cleaning liquid can be maintained, and the temperature of the waste cleaning liquid can be further approximated to the evaporation temperature. That is, in the treatment method of the present invention, the waste cleaning liquid is supplied to the thin film evaporator 7 in a state in which the solid component in the waste cleaning liquid is diffused and viscosity of the waste cleaning liquid is decreased, whereby the blockages in the flow paths and the instruments are prevented. In addition, the waste cleaning liquid is supplied to the thin film evaporator 7 in a state in which the temperature of the waste cleaning liquid is approximated to the evaporation temperature, whereby the function of the thin film evaporator 7 is sufficiently exerted.

In the thin film evaporator 7, the rotating blade 72 is rotated while the waste cleaning liquid is being supplied to the evaporator body 70. Moreover, at that time, the vapor for heating is supplied to the jacket 71, and the evaporator body 70 is heated, for example, to 100 to 130° C. Thus, in the thin film evaporator 7, the thin film of the waste cleaning liquid is formed on the inner surface of the evaporator body 70, and the evaporation of the cleaning liquid is accelerated. In the treatment method of the present invention, as described above, the waste cleaning liquid supplied to the thin film evaporator 7 is stirred and heated to approximate the temperature thereof to the evaporation temperature. Accordingly, the evaporation efficiency in the thin film evaporator 7 can be further increased.

In the thin film evaporator 7, the thin film of the waste cleaning liquid is formed as described above, whereby the cleaning liquid in the waste cleaning liquid is evaporated to separate the solid component. Then, the separated solid component is continuously scrapped off by the rotating blade 72, and is discharged downward from the evaporator body 70 through the sludge discharge port 76. Moreover, the NMP obtained by the evaporation is collected from the vapor outlet 70b in the upper end of the evaporator body 70.

The solid component discharged from the thin film evaporator 7 by such an evaporation separating operation of the thin film evaporator 7, that is, the solid component containing the electrode material is collected to the sludge collection container 8 through the flow path 23. The solid component collected to the sludge collection container 8 can be taken out to the portable container 41 as an example through the unloading line constituted of the flow path 24, the pump 35, and the flow path 25.

Moreover, the vapor collected from the thin film evaporator 7 by the evaporation separating operation of the thin film evaporator 7, that is, the vapor of the NMP is introduced into the condenser 52 through the flow path 16 and is liquefied in the condenser, and in addition, the liquid NMP is reserved in the separated liquid collection container 9 through the flow path 17. Then, the NMP in the separated liquid collection container 9 can be stored in the collected liquid storage tank 42 through the flow path 18, the pump 33, the flow path 19, and the flow path 20. Moreover, when the liquid is fed to the collected liquid storage tank 42, the NMP is cooled down to room temperature by the cooler 53 interposed between the flow path 19 and the flow path 20. The NMP in the collected liquid storage tank 42 can be reused by further being purified by a variety of conventional evaporation methods.

As described above, in the present invention, the waste cleaning liquid is stirred in advance in the stirring tank 6 to evenly diffuse the solid component, and is supplied to the thin film evaporator 7 that is the evaporation separating means in a state in which the solid component is diffused. Accordingly, the solid component can be prevented from being retained and adhered in and to the flow paths and the devices, and the instruments can be prevented from being blocked by the solid component. Moreover, when the waste cleaning liquid is supplied to the thin film evaporator 7, the waste cleaning liquid is heated up to a predetermined temperature in addition to the stirring of the waste cleaning liquid, whereby the viscosity of the waste cleaning liquid is decreased. Accordingly, the solid component can be further suppressed from being retained in the flow paths and the devices. In addition, the temperature of the waste cleaning liquid is raised, whereby the evaporation efficiency in the thin film evaporator 7 can be improved. Accordingly, the separation efficiency of the liquid component and the solid component can be increased, and the high-boiling-point component and the peroxide can be suppressed from being generated. Further, in accordance with the present invention, the volume reduction treatment of the waste liquid becomes more possible, and accordingly, production cost of the electrode can be further reduced.

Note that, similarly to the treatment of the waste cleaning liquid discharged from the positive electrode production process as described above, the present invention can also be applied to treatment of a waste cleaning liquid that is discharged from the negative electrode production process and contains water as a cleaning liquid. Since water can be collected by the evaporation separating means, this can be treated with ease without affecting an environment, and in the same way, the volume reduction treatment of the waste liquid can be further implemented.

EXAMPLES

Example

The waste cleaning liquid discharged from the preparation tank in the positive electrode production process was treated by the apparatus in FIG. 1, and an experiment was performed, in which the NMP was separated and collected, and a residue containing the electrode material was collected. A heat transfer area (a substantial evaporation area) in the evaporator body 70 of the thin film evaporator 7 was set to 0.5 $m^2$. Then, the NMP collected to the separated liquid collection container 9 was weighed, and a volume reduction rate of the waste cleaning liquid was confirmed. Main operation conditions and the volume reduction rate are as shown in Table 1, and blockages in pipes and instruments during the operation were not recognized.

Comparative Example

The waste cleaning liquid discharged from the coating apparatus in the positive electrode production process was supplied to a thin film evaporator 7 similar to that in Example, and was subjected to the evaporation separating treatment. At that time, a conveying line constituted of only flow paths and pumps was used, and the waste cleaning liquid was directly supplied to the thin film evaporator 7 to the portable container 40. Then, after the operation was started, the conveying line was blocked, and a continuous operation was not able to be performed.

TABLE 1

|   | Example 1 | Example 2 |
|---|---|---|
| Treatment amount (ml/min) | 100 to 140 | 160 to 230 |
| Initial temperature of waste cleaning liquid (° C.) | 31 | 33 |
| Operation pressure in system (kPaA) | 6 | 6 |
| Evaporation temperature when supplied to thin film evaporator (° C.) | 135 | 145 |
| Operation temperature of thin film evaporator (° C.) | 95 | 95 |
| Volume reduction rate (%) | 90 | 90 |

INDUSTRIAL APPLICABILITY

The treatment apparatus for waste cleaning liquid and the treatment method for waste cleaning liquid according to the present invention can efficiently separate the liquid component and the solid component from the suspension, can sufficiently collect the liquid component and can subject the liquid component to the volume reduction treatment, and accordingly, are suitable for the treatment of the waste cleaning liquid that is discharged from the process of producing the electrode of the lithium-ion secondary battery and contains the electrode material easy to precipitate.

REFERENCE SIGNS LIST

40 Portable container
41 Portable container
51 Heating device
52 Condenser
53 Cooler
6 Stirring tank
60 Tank body
61 Jacket (heating means)
62 Stirring wing (stirring means)
7 Thin film evaporator (evaporation separating means)
70 Evaporator body
71 Jacket (heating means)
72 Rotating blade
76 Sludge discharge port
8 Sludge collection container
9 Separated liquid collection container

The invention claimed is:

1. A treatment apparatus configured for waste cleaning liquid and configured to treat a waste cleaning liquid discharged from a process of producing an electrode of a lithium-ion secondary battery, the waste cleaning liquid being a suspension of an electrode material that is a solid component and a cleaning liquid, the treatment apparatus comprising:
    a tank body comprising a stirrer configured to stir a waste cleaning liquid introduced from an electrode production process of a lithium-ion secondary battery, the waste cleaning liquid being a suspension of an electrode material that is a solid component and a cleaning liquid;
    a liquid feed line that takes out the waste cleaning liquid from the tank body; and
    an evaporative separator configured to evaporate the cleaning liquid in the waste cleaning liquid to separate a solid component, wherein the evaporative separator is further configured supplied with the waste cleaning liquid by the liquid feed line, wherein a heater capable of heating the waste cleaning liquid in the tank body to a first temperature in a range of from 40 to 90° C. is disposed on an outer circumferential portion of the tank body, and wherein a heating device capable of heating the waste cleaning liquid supplied to the evaporation separator to a second temperature in a range of from 60 to 100° C. is disposed in the liquid feed line.

2. The apparatus of claim 1, wherein the stirrer is stirring wing.

3. The apparatus of claim 1, wherein the tank body comprises a circulation line comprising a pump.

4. The apparatus of claim 1, wherein the evaporative separator is a thin film evaporator.

5. The apparatus of claim 1, wherein the evaporative separator is a thin film evaporator, and wherein the thin film evaporator comprises:
- a cylindrical evaporator body having one end portion from which the waste cleaning liquid is supplied;
- a rotating blade disposed along a centerline of the evaporator body; and
- a heater, disposed on an outer circumferential portion of the evaporator body, and comprising a structure to scrape off, by the rotating blade, a solid component adhered to an inner circumferential surface of the evaporator body and discharge the solid component from other end portion of the evaporator body.

6. The apparatus of claim 1, wherein the cleaning liquid is N-methyl-2-pyrrolidone, and wherein the waste cleaning liquid comprises as a main component, N-methyl-2-pyrrolidone used for cleaning.

7. A method for treating waste cleaning liquid by contacting a waste cleaning liquid discharged from a process of producing an electrode of a lithium-ion secondary battery with the apparatus of claim 1, the method comprising:

stirring, with a stirrer, the waste cleaning liquid, the waste cleaning liquid being a suspension of an electrode material that is a solid component and a cleaning liquid;

supplying the waste cleaning liquid is supplied to the evaporative separator in a state in which the solid component is diffused;

in the evaporative separator, evaporating the cleaning liquid in the waste cleaning liquid to separate the solid component;

heating the waste cleaning liquid in the tank body to the first temperature; and heating the waste cleaning liquid supplied to the evaporative separator to the second temperature.

8. The method of claim 7, wherein the cleaning liquid is N-methyl-2-pyrrolidone, and wherein the waste cleaning liquid comprises, as a main component, N-methyl-2-pyrrolidone that was used for cleaning.

* * * * *